United States Patent [19]

Taguchi et al.

[11] Patent Number: 5,350,692
[45] Date of Patent: Sep. 27, 1994

[54] MICROORGANISMS USEFUL FOR HYDROGEN GAS PRODUCTION

[75] Inventors: Fumiaki Taguchi, Kanagawa; Masayoshi Morimoto, Tokyo; Takeshi Kyoya, Kanagawa; Mikio Takano, Tokyo, all of Japan

[73] Assignee: Kajima Corporation, Tokyo, Japan

[21] Appl. No.: 91,684

[22] Filed: Jul. 15, 1993

Related U.S. Application Data

[62] Division of Ser. No. 787,349, Nov. 4, 1991, abandoned.

[30] Foreign Application Priority Data

Nov. 2, 1990 [JP] Japan ................................. 2-295384

[51] Int. Cl.$^5$ ........................ C12P 3/00; C12N 1/12; C12N 1/20; C12N 1/00
[52] U.S. Cl. ............................. 435/252.7; 435/252.1; 435/168; 435/170; 435/842
[58] Field of Search ................. 435/254, 252.1, 252.7, 435/168, 170, 842

[56] References Cited

PUBLICATIONS

Kinoshita, Noriyoshi et al., *Numazu Kogyo Senmon Gakko Kenkyu Hokoku* 23, pp. 65–70, 1988.
Tanisho et al, Int. J. Hydrogen Energy, 12(9):623–627 (1987) "Fermentative Hydrogen Evolution by Enterobacter Aerogenes Strain E. 82005".
Tanisho et al, Biochimica et Acta, 973 (1989) 1–6 Elsevier, "Hydrogen evolution of Enterobacter aerogenes depending on culture pH: mechanism of hydrogen evolution from NADH by means of membrane-bound hydrogenase".
Tanisho et al, "Enterobacter aerogenes", Hakkokogaku 67:29–34 (1989).
Richard, C., "Genus VI. Enterobacter Hormaeche and Edwards 1960, 72$^{AL}$; Nom. Cons. Opin. 28, Jud. Comm. 1963, 38" in Bergey's Manual of Systematic Bacteriology, 1984, pp. 465–471.

*Primary Examiner*—Douglas W. Robinson
*Assistant Examiner*—Jeffrey J. Seuigny
*Attorney, Agent, or Firm*—Browdy and Neimark

[57] ABSTRACT

The present invention relates to a process for preparing hydrogen gas on an industrial scale by culturing the microorganism *Clostridium beijerinckii* Ferm BP-3592 or the anaerobic asporogenic bacterium strain Ferm BP-3593 in a medium containing glucose and/or a polysaccharide containing a glucose unit.

2 Claims, No Drawings

MICROORGANISMS USEFUL FOR HYDROGEN GAS PRODUCTION

This is a division of application Ser. No. 07/787,349, filed Nov. 4, 1991, now abandoned.

FIELD OF THE INVENTION

The present invention relates to a process for preparing hydrogen gas and, more particularly, a process for preparing hydrogen gas on an industrial scale, using a novel microorganism. The present invention further provides a process for preparing hydrogen gas using a microorganism which uses as a substrate polysaccharides containing a glucose unit as a constituent.

The microorganisms used in the present invention exhibit excellent productivity of hydrogen gas, and thus they are useful for producing hydrogen gas industrially. The present invention, therefore, greatly contributes to the technical field of energy generation. In addition, the microorganisms used in the present invention are also capable of degrading a wide variety of sugars, and the microorganisms are thus useful also for treating waste water discharged in the food industry or in the paper making industry, particularly waste water containing large amounts of sugars. Therefore the present invention also makes a great contribution to the technical fields of waster water treatment and pollution prevention.

BACKGROUND OF THE INVENTION

Description of the Prior Art

In our current industrial society, fossil fuels such as petroleum, coal, natural gas, etc. have been consumed in huge amounts, and this consumption has discharged large quantities of $NO_x$, $SO_x$ and $CO_2$ and the like. This discharge has caused a great number of problems, such as environmental pollution in the form of acid rain, the greenhouse effect in warming the earth, and the like. Further more, it is said that deposits of fossil fuels are limited and will be used up in the near future, causing important social problems.

Accordingly, new clean energy sources free of environmental pollution have been sought as a substitute for fossil fuels have been desired worldwide. Attention has currently focused on alcohol and methane gas as energy sources for the next generation to replace petroleum. However, alcohol and methane gas still present problems, as they produce large amounts of $CO_2$ upon combustion.

Therefore, attention has been directed to hydrogen gas. The exothermic energy per unit weight in combustion for hydrogen gas is three times that of petroleum, and its only by-product is water. It is thus expected that hydrogen gas would be an ideal clean energy source for the next generation.

However, hydrogen gas is currently produced on an industrial scale by means of electrolysis of water, high pressure thermal decomposition of natural gas, and the like. These methods require fossil fuels as energy sources to obtain the hydrogen gas. Unless the problems of energy sources for these methods of obtaining hydrogen gas are solved, the various problems described above, including environmental pollution, are not fundamentally solved.

Currently, attention is paid to microorganisms, and several studies on production of hydrogen gas by microorganisms have been made. Certainly if a method for producing hydrogen gas by microorganisms were established, the method would involve advantages that the system is easily constructed and energy consumption is extremely small, since the reaction is conducted at ambient temperature under ambient pressure. Furthermore, the raw material for producing hydrogen gas is reproducible biomass, and this biomass is obtained by photosynthesis using solar energy. Furthermore, the production of hydrogen gas by microorganisms has another advantage in that environmental pollution is solved due to efficient treatment of waste water, since it is generally possible to use as a raw material an organic substance present in wastes or in waste water.

As described above, several studies were made on the production of hydrogen gas by microorganism and, as a result, some microorganisms capable of producing hydrogen gas were found. These known microorganisms capable of producing hydrogen gas are roughly classified into photosynthetic microorganisms and non-photosynthetic bacteria. The former group includes *Rhodobacter sphaeroides*, which is a photosynthetic bacterium, and Oscillatoria sp. Miami BG7, which is a blue-green algae. The latter includes Azobacter chroococuum and *Klebsiella pneumoniae*, which are nitrogen fixing bacteria, *Escherichia coli* and *Enterobacter aerogenes*, which are facultative anaerobic bacteria, and *Clostridium butyricum*, which is an anaerobic bacterium.

Indeed, the production of hydrogen gas by microorganisms has many advantages as a method for preparing hydrogen gas. However, in practice, this is not practical on an industrial scale. No microorganisms having a suitably high productivity of hydrogen gas that would make it useful on an industrial scale has been found in the studies made so far. As described above, the technique for producing hydrogen gas by microorganisms has not yet reached the industrial level.

None of the currently known microorganisms exhibits good production of hydrogen gas. Photosynthetic microorganisms also require fermenters having a large surface area and large quantities of water for producing hydrogen gas, since solar energy is used.

On the other hand, it is possible to produce hydrogen gas by non-photosynthetic bacteria in a small fermenter. Such a fermenter may be installed underground and, therefore, there is a wide selection of locations for the fermenter. Because non-photosynthetic bacteria do not need solar energy to produce hydrogen gas, there bacteria are more advantageous for producing hydrogen gas than photosynthetic microorganisms.

Among the microorganisms isolated so far, the microorganisms capable of producing hydrogen gas most efficiently is believed to be Enterobacter aerogenes E82005 strain (Tanisho S., et al., *Int. J. Hydrogen Energy* 12, 623, 1987; *Biochim, Biophys, Acta.* 973, 1, 1989). However, this strain is a facultative anaerobic bacterium. The strain also grows under anaerobic conditions, but it grows more actively under aerobic conditions. Therefore, when large quantities of hydrogen are produced in a fermenter, it is difficult to maintain aerobic conditions in the fermenter; namely, the use of this strain is not suitable for industrial production of hydrogen gas.

SUMMARY OF THE INVENTION

It is an object of the present invention to provide newly isolated bacteria that produce hydrogen gas which can utilize polysaccharides as well as glucose as a substrate, and which bacteria are suitable for industrial production of hydrogen gas.

Another object of the present invention is to establish an excellent industrial-grade system for producing hydrogen gas by newly isolated microorganisms which are capable of treating waste water efficiently, particularly waste water abundant in sugars and/or plants.

The present inventors studied means to achieve the objects described above. However, despite extensive investigations from various aspects, they did not achieve success. Therefore, it was necessary to change the conventional concept for screening a microorganisms which can achieve the objects of the present invention.

The present inventors made extensive investigations on the source of microorganism and, as a result, sought the hydrogen-producing bacteria in insects. The present inventors finally succeeded in isolating a novel bacteria having an extremely fast reaction rate and which is capable of producing large quantities of hydrogen gas from *Termites formosans*. Furthermore, it was also surprisingly confirmed that these microorganisms can not only assimilate glucose, but that they also have an extremely high ability to decompose polysaccharides containing glucose as a constituent. In other words, these microorganisms can directly produce hydrogen gas using as a substrate not only monosaccharides such as glucose and the like, but also polysaccharides containing glucose as a constitutent. Such polysaccharide-containing matters, such as organic waste water, can be effectively decomposed. Based upon these effective new findings, the present invention has been accomplished.

That is, as a result of extensive investigations, the present inventors have succeeded in isolating a new hydrogen gas-producing bacterium which can directly produce hydrogen gas using as raw materials not only sugars but also starches. Therefore, the present invention has finally been accomplished.

DETAILED DESCRIPTION OF THE PREFERRED EMBODIMENTS

In order to practice the present invention, it is necessary to isolate anaerobic bacteria from *Termites formosans*. For isolation, for example, live *Termites formosans* are suffocated, and the desired microorganisms are isolated using a medium containing acetic acid salts and formic acid salts. The preferred salts are alkali or alkaline earth metal salts.

For example, the present inventors devised a medium (hereinafter abbreviated as 1/50N+) which was obtained by adding 2.5 g/l each of sodium acetate and sodium formate, which are substrates of methane gas and hydrogen gas, respectively, to a medium is a dilution of nutrient broth (manufactured by Nissui Pharmaceutical Co., Ltd.) to 1/50 (hereinafter abbreviated as 1.50 N), and using the thus obtained medium as the medium for culturing and isolating the bacteria. The inventors also devised oligotrophic 1.50N agar medium by adding 1.5% agar to this 1/50N+ medium. Taking in to account that the present invention will be used for waste water treatment, anaerobic incubation was conducted at 35° C.

In order to isolate and culture anaerobic bacterial efficiently from white ants, or *Termites formosans*, and to culture the bacteria, contact with oxygen was avoided as much as possible. For this reason, live white ants were removed from their nest and were put into a Petri dish. The Petri dish was encased in an anaerobic incubator (Glove Box, manufactured by Forma Co., U.S.A.), and the white ants were suffocated in an anaerobic gaseous mixture of 10% $H_2$, 10% $CO_2$ and 80% $N_2$. Without mashing the suffocated white ants, ten white ants were added to 20 ml of 1/50N+ agar medium. After the mixture was thoroughly mixed by kneading, the mixture was solidified. By this procedure, the white ants were solidified and embedded in agar. Thus, the ants had minimal contact with the gaseous mixture.

Ten agar plate sheets prepared as above were incubated at 35° C. for three weeks under the anaerobic gaseous mixture described above.

Then, by bacterial screening, 153 strains were isolated, and the hydrogen gas productivity of the 153 strains was evaluated. As a result, it was found that 141 strains corresponding to 93% of the 153 strains produced hydrogen gas. Them, an oxygen auxotrophy test was conducted. As a result, eight strains were found to be facultative anaerobic bacteria. Finally, the present inventors succeeded in isolating two candidates, namely, AM21B and AM37F, which were found suitable for the purpose of the present invention.

Among the microorganisms isolated to date, *Enterobacter aerogenes* E82005 strain was believed to produce hydrogen gas most efficiently, as described above. This strain produces 11 mmol of medium hour. The two best strains isolated by the present invention have a productivity of hydrogen gas which is much higher than the known strain, as will be later described Based upon the properties of these strains (according to API 20A, Rap ANA II system), AM21B has been identified to be Clostridium beijerinckii and AM37F was found to be a new hydrogen producing bacterium which was impossible to identify. In more detail, AM437F is gram positive, rod, asporogenic anaerobic and is capable of producing hydrogen gas. No bacterium having such characteristics has not heretofore been reported, and AM37F is quite novel.

The present inventors have investigated the starch degradation ability and the gas productivity of the novel bacteria described above, and succeeded in providing the process of the present invention for preparing hydrogen gas using this novel bacterium, The present invention provides a process for preparing hydrogen gas which comprises culturing the hydrogen gas-producing bacteria, sing a monosaccharide and/or a polysaccharide substrate containing a glucose unit. As the hydrogen gas-producing bacterium, AM21B or AM37F described above may be used.

AM21B and AM37F strains were deposited in the Fermentation Research Institute of the Agency of Industrial Science and Technology of Japan under the deposit numbers FERM BP-3592 and FERM BP-3593, respectively.

The general properties, biochemical properties, enzyme activity and hydrogen gas productivity of AM21B and AM37F are shown in Tables 1, 2, 3 and 4.

| TABLE 1 |
|---|
| GENERAL PROPERTY |
| Growth Ability |

TABLE 1-continued

| Strain | Gram Staining | Shape | Mobility | Spore | Oxygen Auxo-trophy | Peptone Water | Glucose-Added Peptone Water |
|---|---|---|---|---|---|---|---|
| AM21B | positive | rod | mobile | yes | no* | — | + |
| AM37F | positive | rod | mobile | no | no* | — | + |

*anaerobic

TABLE 2

| BIOCHEMICAL PROPERTY | | |
|---|---|---|
| Strain | AM21B | AM37F |
| Indole | — | — |
| Urease | — | — |
| Glucose | + | + |
| Mannitol | + | + |
| Lactose | + | + |
| Sucrose | + | + |
| Maltose | + | + |
| Salicin | + | + |
| Xylose | + | + |
| Arabinose | + | + |
| Gelatin | — | — |
| Esculin | + | + |
| Glycerine | + | — |
| Cellobiose | + | + |
| Mannose | + | + |
| Melezitose | + | — |
| Raffinose | + | + |
| Sorbitol | + | — |
| Ramnose | + | — |
| Trehalose | + | + |
| Catalase | — | — |

TABLE 3

| ENZYME ACTIVITY | | |
|---|---|---|
| Strain | AM21B | AM37F |
| α-arabinosidase | — | — |
| β-galactosidase | — | — |
| α-glucosidase | + | ++++ |
| β-glucosidase | + | — |
| α-galactosidase | — | ++++ |
| α-fucosidase | — | — |
| N-acetylglucosaminidase | — | — |
| alkaline phosphatase | — | — |
| leucylglycine aminopeptidase | — | — |
| glycine aminopeptidase | — | — |
| proline aminopetidase | — | — |
| phenylalanine aminopeptidase | — | — |
| arginine aminopeptidase | — | — |
| serine aminopeptidase | — | — |
| pyrrolidone aminopeptidase | — | — |
| tryptophanase | — | — |

TABLE 4

| Strain | Hydrogen Gas Productivity (ml $H_2$/l · hr) | |
|---|---|---|
| E. aerogenes E82005* | 246 ml | 1.0 (index for producing hydrogen gas) |
| AM37F | 2,790 | 11.3 |
| AM21B | 2,515 | 10.2 |

*Tanisho S., Int. J. Hydrogen Energy 12: 623 1987
Biochem. Biophys. Acta, 973, 1, 1989.

As stated above, *Enterobacter aerogenes* E82005 strain showed a hydrogen gas production of 246 ml/1.hr, whereas the hydrogen gas production of the two strains which were successfully isolated from white ants by the present inventors exhibited a hydrogen gas productivity of from ten to eleven times that of the E82005 strain. This means that the two strains of the present invention are suitable for industrial production of hydrogen gas.

The present invention is described by reference to the examples.

EXAMPLE 1

Carbon source-free PY liquid medium [1% peptone, manufactured by Eiken Chemical Co, 0.5% yeast extract, manufactured by Nissui Pharmaceutical Co.] was combined with 0.5% of either PYG or PYS liquid medium obtained by supplementing glucose or starch, respectively, (manufactured by Difco) as a carbon source to the PY liquid medium. Three ml. of PYG or PYS medium was added to a small test tube with a Dahram tube, and sterilized in an autoclave. After it was confirmed that no bubbles remained in the Dahram tubes, AM21B or AM37F was inoculated on the medium and cultured in an anaerobic incubator in an anaerobic gaseous mixture composed of 10% $CO_2$, 10% $H_2$ and 80% $N_2$ at 35° C. overnight, whereupon growth of the bacteria and the presence or absence of a bubble in the Dahram tube were observed. Where gas was observed in the Dahram tube, it was assumed that hydrogen gas was present by its explosion in a combustion test.

The role of starch as the carbon source was evaluated. The results are shown in Table 5. The novel strains obtained by the present inventors did no grow in peptone alone, but also grew well when the peptone was supplemented by glucose or yeast extract. When glucose or starch was added to PY medium, it was noted that all bacteria tested grew well and, at the same time, produced gas (hydrogen gas) which burned with an explosion. With respect to bacteria which hydrolyze starch, although many reports have been made so far, no bacteria capable of producing hydrogen gas directly from starch has not been heretofore reported. This is the first such report.

TABLE 5

| Strain | P Growth | P Gas | PG Growth | PG Gas | PY Growth | PY Gas | PYG Growth | PYG Gas | PYS Growth | PYS Gas |
|---|---|---|---|---|---|---|---|---|---|---|
| AM21B | — | — | + | + | + | — | + | + | + | + |
| AM37F | — | — | + | + | + | — | + | + | + | + |

In Table 5:

Growth+indicates the state of good growth and turbidity;

Gas+indicates that gas was produced and filled the Dabram tube (2.5 cm long)

EXAMPLE 2

GAM bouillon medium containing 0.3% glucose and 0.5% starch. PYG medium containing 1.0% glucose and PYS medium containing 1.0% starch were prepared in quantities of 1000 ml each. AM21B or AM37F were inoculated on each medium, respectively, whereby the gas produced was measured. The composition of the gas was analyzed by gas chromatography.

The results are shown in Table 6. It was confirmed that both AM21B and AM37F strains produced hydrogen gas from starch and almost the same level as from glucose.

GAM #1 is GAM bouillon manufactured by Nissui Pharmaceutical Co., Ltd. and contains 0.3% glucose and 0.5% starch.

GAM #2 is GAM #1 to which has been added 0.7% glucose.

PY is an aqueous meditan containing 1% peptone and 0.5% yeast extract.

As can be clearly seen from Table 7, AM21B strain

TABLE 6

| Strain | | Additive (%) Glucose | Starch | Total Gas produced (ml) | Rate of Gas produced (ml/hr) | Hydrogen gas (ml) | Rate of Hydrogen Gas produced (ml/hr) |
|---|---|---|---|---|---|---|---|
| AM21B | GAM | 0.3 | 0.5 | 2900 | 850 | 1200 | 340 |
| | PYG | 1.0 | 0 | 3000 | 650 | 1000 | 210 |
| | PYS | 0 | 1.0 | 3000 | 585 | 900 | 180 |
| AM37F | GAM | 0.3 | 0.5 | 2800 | 820 | 1150 | 336 |
| | PYG | 1.0 | 0 | 2600 | 610 | 860 | 200 |
| | PHY | 0 | 1.0 | 2400 | 480 | 720 | 150 |

EXAMPLE 3

GAM bouillon #1 (containing 0.3% glucose and 0.5% starch), GAM bouillon #2 containing 1% glucose prepared by adding 0.7% glucose or starch to GAM bouillon #1 and medium PY ##to PY#7 by adding glucose or starch to PY medium in an appropriate proportion were prepared in quantities of 1000 ml each. AM21B strain was inoculated on each medium followed by spinner culture in a thermostat at 36° C. The amount of gas evolved was measured. Based upon the concentration of hydrogen gas obtained from a compositional analysis of the gas, the amount of hydrogen gas produced was calculated. The results are shown in Table 7.

TABLE 7

| Basal Medium | Additive (%) Glucose | Starch | Total Gas Produced (ml) | Rate of Gas Produced (ml/hr) | Hydrogen Gas (ml) | Rate of Hydrogen Gas Produced (ml/hr) |
|---|---|---|---|---|---|---|
| GAM #1 | 0.3 | 0.5 | 2900 | 850 | 1200 | 340 |
| GAM #2 | 1.0 | 0.5 | 4700 | 970 | 2100 | 430 |
| PY #3 | 1.0 | 0 | 3000 | 650 | 1000 | 210 |
| PY #4 | 1.0 | 1.0 | 4200 | 690 | 2400 | 400 |
| PY #5 | 0.3 | 0.5 | 2600 | 500 | 1360 | 230 |
| PY #6 | 0 | 0.5 | 1500 | 405 | 830 | 224 |
| PY #7 | 0 | 1.0 | 3000 | 585 | 950 | 190 | produced 1500 ml and 3000 ml. of gas, respectively, in PY #6 and PY #7 containing starch alone. It was confirmed that when the concentration of the starch was doubled (from 0.5 to 1%), the amount of gas produced doubled. From GAM #1 and PY #5, the amounts of gas produced, 2900 ml and 2600 ml, were noted, respectively. From PY #3 and PY #7, 3000 ml. of gas was produced. It was thus confirmed that the new strain described above was extremely efficient in producing hydrogen gas from starch.

As is evident from these results according to the present invention, hydrogen gas can be produced directly in large quantities not only from monosaccharides as a substrate, but also from polysaccharides. It is not too much to say that a method for industrial production of hydrogen gas has been established by the present invention for the first time.

These results also reveal that in treating natural matters containing sugar or which are composed of sugar, these bacterial strains are very effective. The strains may be used also for clarifying juice or various agricultural products, reducing viscosity and increasing fluidity. These strains are especially useful for treating organic waste waters discharged from beet factories or orange processing factories and other waste waters containing organic substances such as pulp plant fibers, starch, and polysaccharides. It is also possible to apply the present invention to environmental purification by treating waste waters and liquid wastes.

We claim:
1. A biologically pure culture of clostridium beijerinckii FERM BP-3592.
2. A biologically pure culture of bacterium strain FERM BP-3593.

* * * * *